(12) United States Patent
Tezuka et al.

(10) Patent No.: US 9,890,360 B2
(45) Date of Patent: Feb. 13, 2018

(54) METHOD FOR PRODUCING INDUCED PLURIPOTENT STEM CELLS

(71) Applicants: GIFU UNIVERSITY, Gifu-shi, Gifu (JP); NATIONAL INSTITUTE OF ADVANCED INDUSTRIAL SCIENCE AND TECHNOLOGY, Tokyo (JP)

(72) Inventors: Kenichi Tezuka, Gifu (JP); Naritaka Tamaoki, Gifu (JP); Kazuki Iida, Gifu (JP); Tomoko Kawaguchi, Gifu (JP); Hitomi Aoki, Gifu (JP); Takahiro Kunisada, Gifu (JP); Toshiyuki Shibata, Gifu (JP); Naoki Goshima, Tokyo (JP)

(73) Assignees: GIFU UNIVERSITY, Gifu-shi (JP); NATIONAL INSTITUTE OF ADVANCED INDUSTRIAL SCIENCE AND TECHNOLOGY, Tokyo (JP)

( * ) Notice: Subject to any disclaimer, the term of this patent is extended or adjusted under 35 U.S.C. 154(b) by 0 days.

(21) Appl. No.: 14/914,986

(22) PCT Filed: Aug. 28, 2014

(86) PCT No.: PCT/JP2014/072564
§ 371 (c)(1),
(2) Date: Feb. 26, 2016

(87) PCT Pub. No.: WO2015/030111
PCT Pub. Date: Mar. 5, 2015

(65) Prior Publication Data
US 2016/0208218 A1    Jul. 21, 2016

(30) Foreign Application Priority Data
Aug. 28, 2013 (JP) ................... 2013-176647

(51) Int. Cl.
*C12N 5/00* (2006.01)
*C12N 5/074* (2010.01)

(52) U.S. Cl.
CPC ........ *C12N 5/0696* (2013.01); *C12N 2501/40* (2013.01); *C12N 2501/60* (2013.01); *C12N 2501/602* (2013.01); *C12N 2501/603* (2013.01); *C12N 2501/604* (2013.01); *C12N 2501/606* (2013.01); *C12N 2506/1361* (2013.01); *C12N 2510/00* (2013.01)

(58) Field of Classification Search
None
See application file for complete search history.

(56) References Cited

U.S. PATENT DOCUMENTS

2013/0022583 A1*  1/2013  Wernig ............... C12N 5/0619
424/93.7

FOREIGN PATENT DOCUMENTS

| JP | 2011-529330 A | 12/2011 |
|---|---|---|
| WO | 2009/133971 A1 | 11/2009 |
| WO | 2010/013359 A1 | 2/2010 |
| WO | 2013/022022 A1 | 2/2013 |

OTHER PUBLICATIONS

Robinton and Daley. The Promise of Induced Pluripotent Stem Cells in Research and Therapy. Nature, 2012. 481:295-305.*
Maekawa, Momoko et al., "Direct reprogramming of somatic cells is promoted by maternal transcription factor Glis1," Nature, vol. 474, Jun. 9, 2011, pp. 225-230.
Trinh, BQ et al., "Homeodomain protein DLX4 counteracts key transcriptional control mechanisms of the TGF-beta cytostatic program and blocks the antiproliferative effect of TGF-beta," Oncogene, (2011), vol. 30, pp. 2718-2729.
Trinh, Bon Q et al., "Abstract B15: The homeobox patterning gene DLX4 confers resistance to transfomring growth factor-beta signaling in tumors," Cancer Research, Sep. 15, 2011.
Tomaoki, N. et al., Regenerative Medicine, (2014), vol. 13 (suppl.), pp. 227.
Gopinathan, Gokul et al., "Epigenetic Marks Define the Lineage and Differentiation Potential of Two Didtinct Neural Crest-Derived Intermediate Odontogenic Progenitor Populations," Stem Cells and Development, vol. 22, No. 12, (2013), pp. 1763-1778.
Dinger, Marcel E. et al., "Long noncoding RNAs in mouse embryonic stem cell pluripotency and differentiation," Genome Research, (2008), vol. 18, pp. 1433-1445.
Holland, Peter WH et al., "Classification and nomenclature of all human homeobox genes," BMC Biology, (2007), vol. 5, No. 47, pp. 1-28.
Tomaoki, Naritaka et al., "The homeobox gene DLX4 promotes generation of human induced pluripotent stem cells," Scientific Reports, (2014), vol. 4.
Mar. 3, 2015 International Preliminary Report on Patentability issued in International Patent Application No. PCT/JP2014/072564.
Nov. 20, 2014 Written Opinion issued in International Patent Application No. PCT/JP2014/072564.
Dec. 2, 2014 Search Report issued in International Patent Application No. PCT/JP2014/072564.
Jan. 26, 2017 Search Report issued in European Patent Application No. 14839864.7.
Liu et al; "Expression Pattern of Oct-4, Sox2, and c-Myc in the Primary Culture of Human Dental Pulp Derived Cells;" Journal of Endodontics; vol. 37; No. 4; Apr. 4, 2011; pp. 466-472.
Quinn L Metal; "Isolation and identification of homeobox genes from the human placenta including a novel member of the Distal-less family, DLX4;" Gene, Elsevier, Amsterdam, NL.; vol. 187; No. 1; Mar. 10, 1997; pp. 55-61.
Shimamoto et al; "Overexpression of the homeobox gene DLX-7 inhibits apoptosis by induced expression of intercellular adhesion molecule-1;" Experimental Hematology; vol. 28; No. 4; Apr. 1, 2000; pp. 433-441.

* cited by examiner

*Primary Examiner* — Christopher M Babic
*Assistant Examiner* — Kimberly A Aron
(74) *Attorney, Agent, or Firm* — Oliff PLC

(57) ABSTRACT

A method that includes bringing a nuclear reprogramming substance (DLX4 gene, OCT3/4 gene, and SOX2 gene) into contact with a cell and thereby producing iPS cells.

7 Claims, 8 Drawing Sheets

SEQUENCE LISTING

<160> NUMBER OF SEQ ID NOS: 8

<210> SEQ ID NO 1
<211> LENGTH: 723
<212> TYPE: DNA

<213> ORGANISM: Homo sapiens

<400> SEQUENCE: 1

```
atgacctctt tgccctgccc cctccccggc cgggacgcct ccaaagctgt cttcccagac     60
ctcgccctg  tccgtcggt  agcggctgcc  tacccgcttg  gcttgtcccc  tacaaccgca    120
gcctccccca  atttgtccta  ctccaggccg  tatggccacc  tcctgtctta  ccctacacc    180
gagccagcga  accccggaga  ctcctacctg  tcctgccagc  aacccgcggc  gctctctcag    240
cccctctgcg  gacctgcaga  gcaccctcag  gaactcgagg  cagactcgga  gaagccgcgg    300
ctgtccccgg  aaccctccga  gcggcgccct  caggccccg   ccaaaaagct  ccgcaagccg    360
aggaccatct  actccagcct  gcagctgcag  cacctaaacc  agcgtttcca  gcacacgcag    420
tacctggcgc  tgcccgagag  ggcccagctg  gcagcgcagc  tcggcctcac  ccagacccag    480
gtaaagatct  ggtttcagaa  caaacgctcc  aagtataaga  agctcctgaa  gcagaattct    540
gggggggcagg  aagggacctt  ccctgggagg  accttctctg  tgtctccctg  ctccccaccc    600
ctcccctccc  tctgggatct  acccaaggca  gggaccctgc  ccaccagtgg  ctatggcaac    660
agctttggag  cctggtatca  gcatcactcc  tcagatgtcc  tggcttcgcc  tcagatgatg    720
tag                                                                    723
```

<210> SEQ ID NO 2
<211> LENGTH: 240
<212> TYPE: PRT
<213> ORGANISM: Homo sapiens

<400> SEQUENCE: 2

```
Met Thr Ser Leu Pro Cys Pro Leu Pro Gly Arg Asp Ala Ser Lys Ala
1               5                   10                  15

Val Phe Pro Asp Leu Ala Pro Val Pro Ser Val Ala Ala Tyr Pro
            20                  25                  30

Leu Gly Leu Ser Pro Thr Thr Ala Ala Ser Pro Asn Leu Ser Tyr Ser
        35                  40                  45

Arg Pro Tyr Gly His Leu Leu Ser Tyr Pro Tyr Thr Glu Pro Ala Asn
    50                  55                  60

Pro Gly Asp Ser Tyr Leu Ser Cys Gln Gln Pro Ala Ala Leu Ser Gln
65                  70                  75                  80

Pro Leu Cys Gly Pro Ala Glu His Pro Gln Glu Leu Glu Ala Asp Ser
                85                  90                  95

Glu Lys Pro Arg Leu Ser Pro Glu Pro Ser Glu Arg Arg Pro Gln Ala
            100                 105                 110

Pro Ala Lys Lys Leu Arg Lys Pro Arg Thr Ile Tyr Ser Ser Leu Gln
        115                 120                 125

Leu Gln His Leu Asn Gln Arg Phe Gln His Thr Gln Tyr Leu Ala Leu
    130                 135                 140

Pro Glu Arg Ala Gln Leu Ala Ala Gln Leu Gly Leu Thr Gln Thr Gln
145                 150                 155                 160

Val Lys Ile Trp Phe Gln Asn Lys Arg Ser Lys Tyr Lys Lys Leu Leu
                165                 170                 175

Lys Gln Asn Ser Gly Gly Gln Glu Gly Asp Phe Pro Gly Arg Thr Phe
            180                 185                 190

Ser Val Ser Pro Cys Ser Pro Leu Pro Ser Leu Trp Asp Leu Pro
        195                 200                 205

Lys Ala Gly Thr Leu Pro Thr Ser Gly Tyr Gly Asn Ser Phe Gly Ala
    210                 215                 220
```

Trp Tyr Gln His His Ser Ser Asp Val Leu Ala Ser Pro Gln Met Met
225                 230                 235                 240

<210> SEQ ID NO 3
<211> LENGTH: 814
<212> TYPE: DNA
<213> ORGANISM: Mus musculus

<400> SEQUENCE: 3

```
atgacctctt taccctgtcc ccttcctgac cgtggtgcct ccaacgttgt cttcccggac      60
ctcgccccg ccctgtcggt agtggctgct tacccgctcg gactatcccc gggaaccgca     120
gcttctcccg atttgtccta ctcccaatcc tacggccacc cccgtcctta ttcccaccct     180
gggccggcaa ccccaggaga ctcctacctg ccccgccagc aacaattggt ggcgccatct     240
cagccctttc acaggccggc tgaacacccg caggaactcg aagcagaatc ggagaagctg     300
gcactgtctc tggtgccctc ccagcagcag tccctgacca ggaagctgcg caagcccaga     360
accatctact ctagcctgca gctccaacac ctgaaccagc gtttccagca cacccaatac     420
ctggccctgc ccgagagagc tcagctggca gcacaactcg gactcaccca aacccaggta     480
aagatctggt ttcagaacaa cgctccaaa tataagaagc tcctgaaaca gagctctggg     540
gagccggaag aggacttctc tgggagaccc cctccctgt ctccccactc tccagcccta     600
ccattcatct ggggtctacc caaggcagac acctgccctt ccagtggcta tgacaacagc     660
cactttggtg cctggtatca gcatcgctcc ccagatgtgc tggcactgcc tcagatgatg     720
tgagtctgga gggaggctgg tcagacttca gccctcctgt caagcccagg acccgagcac     780
ctgctcccct tctgggagga gaggaaacca gctc                                 814
```

<210> SEQ ID NO 4
<211> LENGTH: 240
<212> TYPE: PRT
<213> ORGANISM: Mus musculus

<400> SEQUENCE: 4

Met Thr Ser Leu Pro Cys Pro Leu Pro Asp Arg Gly Ala Ser Asn Val
1               5                   10                  15

Val Phe Pro Asp Leu Ala Pro Ala Leu Ser Val Val Ala Ala Tyr Pro
            20                  25                  30

Leu Gly Leu Ser Pro Gly Thr Ala Ala Ser Pro Asp Leu Ser Tyr Ser
        35                  40                  45

Gln Ser Tyr Gly His Pro Arg Ser Tyr Ser His Pro Gly Pro Ala Thr
    50                  55                  60

Pro Gly Asp Ser Tyr Leu Pro Arg Gln Gln Gln Leu Val Ala Pro Ser
65                  70                  75                  80

Gln Pro Phe His Arg Pro Ala Glu His Pro Gln Glu Leu Glu Ala Glu
                85                  90                  95

Ser Glu Lys Leu Ala Leu Ser Leu Val Pro Ser Gln Gln Gln Ser Leu
            100                 105                 110

Thr Arg Lys Leu Arg Lys Pro Arg Thr Ile Tyr Ser Ser Leu Gln Leu
        115                 120                 125

Gln His Leu Asn Gln Arg Phe Gln His Thr Gln Tyr Leu Ala Leu Pro
    130                 135                 140

Glu Arg Ala Gln Leu Ala Ala Gln Leu Gly Leu Thr Gln Thr Gln Val
145                 150                 155                 160

Lys Ile Trp Phe Gln Asn Lys Arg Ser Lys Tyr Lys Lys Leu Leu Lys

```
                    165                 170                 175
Gln Ser Ser Gly Glu Pro Glu Glu Asp Phe Ser Gly Arg Pro Pro Ser
            180                 185                 190

Leu Ser Pro His Ser Pro Ala Leu Pro Phe Ile Trp Gly Leu Pro Lys
        195                 200                 205

Ala Asp Thr Leu Pro Ser Ser Gly Tyr Asp Asn Ser His Phe Gly Ala
    210                 215                 220

Trp Tyr Gln His Arg Ser Pro Asp Val Leu Ala Leu Pro Gln Met Met
225                 230                 235                 240

<210> SEQ ID NO 5
<211> LENGTH: 20
<212> TYPE: DNA
<213> ORGANISM: Artificial Sequence
<220> FEATURE:
<223> OTHER INFORMATION: Primer

<400> SEQUENCE: 5
taaaccagcg tttccagcac                                           20

<210> SEQ ID NO 6
<211> LENGTH: 25
<212> TYPE: DNA
<213> ORGANISM: Artificial Sequence
<220> FEATURE:
<223> OTHER INFORMATION: Primer

<400> SEQUENCE: 6
cttatacttg gagcgtttgt tctga                                     25

<210> SEQ ID NO 7
<211> LENGTH: 19
<212> TYPE: DNA
<213> ORGANISM: Artificial Sequence
<220> FEATURE:
<223> OTHER INFORMATION: SiRNA

<400> SEQUENCE: 7
gaaacctggt aaagtaaca                                            19

<210> SEQ ID NO 8
<211> LENGTH: 19
<212> TYPE: DNA
<213> ORGANISM: Artificial Sequence
<220> FEATURE:
<223> OTHER INFORMATION: SiRNA

<400> SEQUENCE: 8
cgaattggag cttgagctt                                            19
```

METHOD FOR PRODUCING INDUCED PLURIPOTENT STEM CELLS

TECHNICAL FIELD

This application relates to Japanese Patent Application No. 2013-176647 filed on Aug. 28, 2013 and claims priority to the Japanese Patent Application, the contents of which are incorporated herein by reference in their entirety.

The specification relates to production of induces pluripotent stem cells.

BACKGROUND ART

It has been conventionally known that four factors (an OCT3/4 gene, an SOX2 gene, a KLF4 gene, and a c-MYC gene) as nuclear reprogramming substances are transfected into a somatic cell to produce iPS cells (induced pluripotent stem cells). However, among the four factors, for example, the c-MYC gene can be a risk of tumor formation and thus is desired not to be used. That is, it is required to consider the combination of nuclear reprogramming substances.

In the Patent Literature 1, three factors (an OCT3/4 gene, a SOX2 gene, and KLF4 gene) as nuclear reprogramming substances are brought into contact with a pulpal stem cell to produce iPS cells. In the Non-Patent Literature 1, four factors (an OCT3/4 gene, an SOX2 gene, a KLF4 gene, and a Glis1 gene) as nuclear reprogramming substances are transfected into a somatic cell to produce iPS cells.

Patent Literature 1: WO 2010/013359

Non-Patent Literature 1: Momoko Maekawa et al., Nature, vol. 474, 225-229

SUMMARY OF INVENTION

The present specification discloses a method for producing iPS cells with superior induction efficiency by using a novel combination of nuclear reprogramming substances.

Solution to Technical Problem

The inventors of the present invention found that the iPS cell induction efficiency is increased by bringing three factors (an OCT3/4 gene, an SOX2 gene, and a KLF4 gene) as nuclear reprogramming substances into contact with a certain type of DPC (Dental Pulp Cell, pulp cell). Furthermore, the inventors of the present invention found that a DLX4 gene is highly expressed in the DPC. Thus, the inventors of the present invention could produce iPS cells using nuclear reprogramming substances including the DLX4 gene and obtained the iPS cells efficiently. That is, the disclosure of the present specification is based on the production of iPS cells using nuclear reprogramming substances including the DLX4 gene and the evaluation of the induction efficiency by the inventors of the present invention.

(1) A method for producing induced pluripotent stem cells, comprising:
bringing a nuclear reprogramming substance including at least a DLX4 gene or a translation product thereof into contact with a cell.
(2) The method according to (1), wherein
the nuclear reprogramming substance further includes a gene in an OCT family or a translation product thereof, and a gene in an SOX family or a translation product thereof.
(3) The method according to (1), wherein
the nuclear reprogramming substance further includes a gene in a KLF4 family or a translation product thereof.
(4) The method according to (2), wherein
the nuclear reprogramming substance further includes a gene in a KLF4 family or a translation product thereof.
(5) The method according to any one of (1) to (4), wherein
the cell comprises a pulp cell.
(6) The method according to (2), wherein
the cell comprises a pulp cell.
(7) The method according to (5), wherein
the pulp cell comprises a pulp cell before a stage of completion of tooth root formation.
(8) The method according to (6), wherein
the pulp cell comprises a pulp cell before a stage of completion of tooth root formation.
(9) A vector set comprising one or two or more recombinant vectors which retains a DLX4 gene, an OCT3/4 gene and an SOX2 gene.

DESCRIPTION OF EMBODIMENTS

Figure 1:
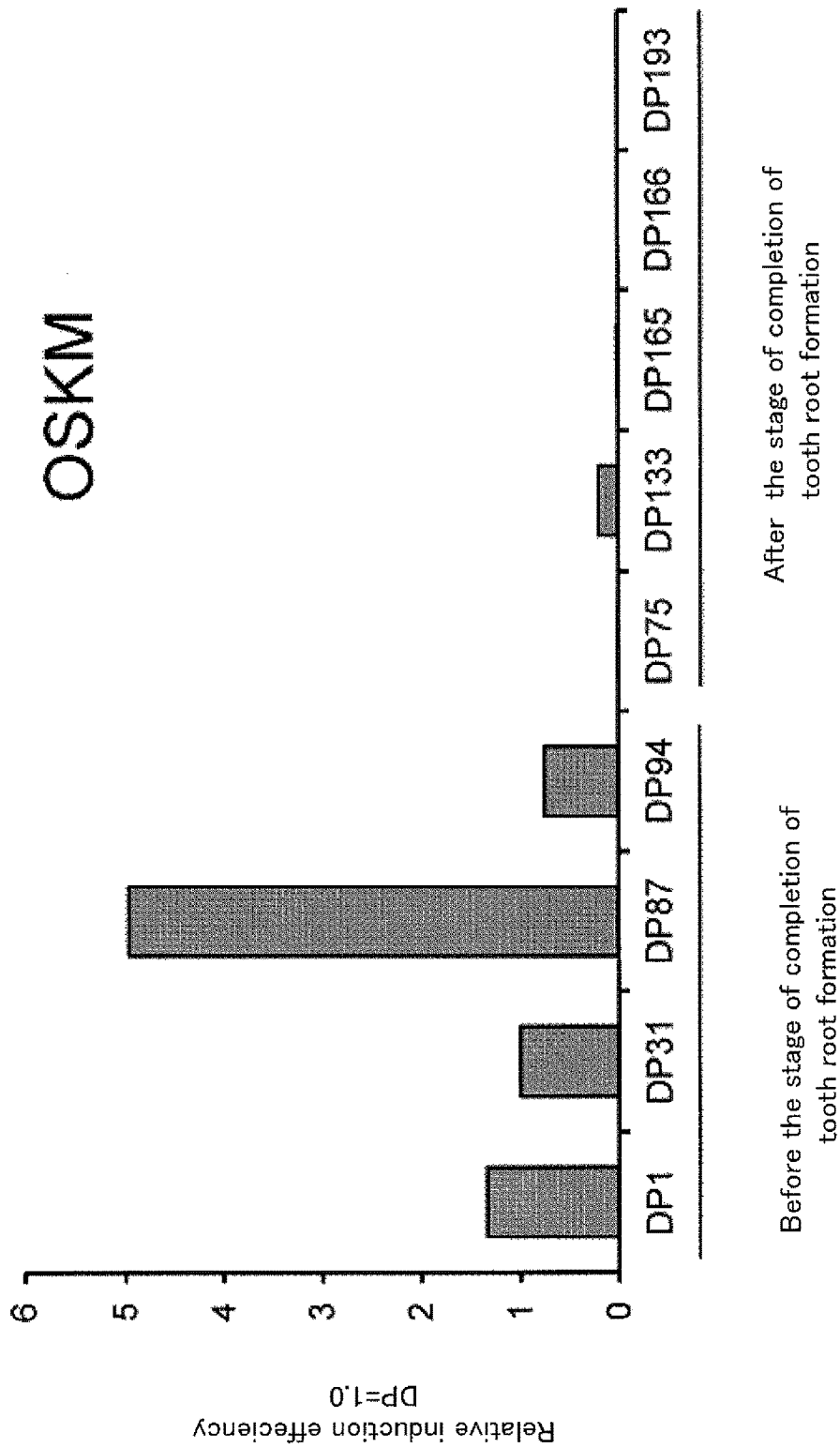
FIG. 1 shows a relative reprogramming efficiency in each DPC.

The present specification relates to the production of iPS cells using the DLX4 gene or the translation product thereof. It has not been known that the expression in a somatic cell of the DLX4 gene is involved in the induction of iPS cells from the somatic cell. According to the disclosure of the present specification, iPS cells can be produced with superior induction efficiency. Moreover, the somatic cell in which the expression of DLX4 gene is accelerated is suitable for the induction of iPS cells. By using such somatic cell, iPS cells can be produced with further superior induction efficiency.

According to the disclosure of the present specification, a nuclear reprogramming substance, a DLX4 gene, a recombinant vector, a vector set, a cell, a DPC, an iPS cell production agent, a method for producing iPS cells, and the like are described in order in detail below.

(Nuclear Reprogramming Substance)

The present specification discloses nuclear reprogramming substances. The nuclear reprogramming substances are substances which reprogram the nucleus of the somatic cell to induce the pluripotency.

Representative and non-limiting specific embodiments of the present disclosure are described in detail with reference to the drawings as appropriate. This detailed description is merely intended to indicate details for implementing preferred embodiments of the present invention, to a person skilled in the art, and is not intended to limit the scope of the present disclosure. Furthermore, additional features and invention(s) disclosed below can be used separately from or jointly with other features and invention(s), in order to provide a further improved method for producing induced pluripotent stem cells.

Moreover, the combination of features and steps disclosed in the following detailed description is not essential for implementing the present disclosure in the broadest sense, and are described only for specifically describing representative specific embodiments of the present disclosure. Furthermore, various features of the representative specific embodiments described above and below and various features described in the independent and dependent claims do not have to be combined as described in the specific embodiments given here or in the listed order, in order to provide additional and useful embodiments of the present disclosure.

All of the features described in the present specification and/or claims are intended to be disclosed individually or independently from each other as limitations of the specific matters disclosed and claimed as originally filed, separately from the composition of features described in the embodiments and/or claims. Furthermore, all of the numerical ranges and descriptions of groups or groupings are intended to disclose intermediate compositions, as limitations of the specific matters disclosed and claimed as originally filed.

(DLX4 Gene)

The nuclear reprogramming substance disclosed in the present specification includes at least a DLX4 gene. The DLX4 gene can effectively enhance the iPS cell induction efficiency. More specifically, by combining with the gene belonging to the SOX family including an SOX2 gene and the gene belonging to the OCT family including an OCT3/4 gene, the iPS cell induction efficiency can be certainly and dramatically enhanced. Moreover, the DLX4 gene can further enhance the iPS cell induction efficiency by a synergistic effect specifically with the gene belonging to the KLF family such as a KLF4 gene.

The expression of DLX4 gene is accelerated in a pulp cell, specifically before the stage of the completion of tooth root formation. Therefore, as mentioned below, by specifically using the pulp cell before the stage of the completion of tooth root formation as a target cell, the DLX4 can further enhance the iPS cell induction efficiency gene further effectively.

As the DLX4 gene, for example, a human-derived DLX4 gene can be used. As the human-derived DLX4 gene, DNA having a base sequence represented by SEQ ID NO: 1 can be used. As a mouse-derived DLX4 gene, DNA having a base sequence represented by SEQ ID NO: 3 can be used. A DLX4 protein (Distal-less homeobox 4, also referred to as or BPI) which is a translation product of the DLX4 gene is a transcription factor having a homeodomain and is known to suppress transcription of a β-globin gene (Mol. Cell. Biol. 22, 2505-2514, 2002). Moreover, DLX1 to DLX7 genes are known as genes in the DLX gene family. In the technology disclosed in the present specification, not only the DLX4 gene, but also these genes in this family can be used alone or in a combination as long as having the same function as the DLX4 gene.

The nuclear reprogramming substance can further include the gene belonging to the OCT family and the gene belonging to the SOX family. The nuclear reprogramming substance can further include the gene belonging to the KLF family. The nuclear reprogramming substance may further include other genes. Hereinafter, a plurality of genes which are nuclear reprogramming substances are also merely referred to as genes. Moreover, the gene in the present specification intends a nucleic acid (preferably DNA) which encodes a protein which is a translation product of the gene. Considering the ease of transfection into a cell, the nuclear reprogramming substance is preferably used not as a protein itself which is the translation product thereof but as a gene which encodes the protein.

(OCT Family Gene)

The gene in the OCT family can be an OCT3/4 gene, an OCT1A gene, an OCT6 gene, or the like. These genes in the OCT family may be used alone or in a combination of two or more of them. From the viewpoint of the efficient induction of iPS cells, the OCT3/4 gene is favorably used among the genes in the OCT family. The base sequences of the OCT3/4 gene are publicly known (NCBI accession Nos. NM_002701 (human) and NM_013633 (Mouse)). Moreover, the base sequences of the OCT1A gene are publicly known (NCBI accession Nos. NM_002697 (human) and NM_198934 (Mouse)), and the base sequences of the OCT6 gene are publicly known (NCBI accession Nos. NM_002699 (human) and NM_011141 (Mouse)).

(SOX2 Family)

The gene in the SOX family can be an SOX1 gene, an SOX2 gene, an SOX3 gene, an SOX7 gene, an SOX15 gene, an SOX17 gene, or an SOX18 gene. These genes in the SOX family may be used alone or in a combination of two or more of them. From the viewpoint of the efficient induction of iPS cells, the SOX2 gene is favorably used among the genes in the SOX family. Moreover, the base sequences of the SOX2 gene are publicly known (NCBI accession Nos. NM_003106 (human) and NM_011443 (Mouse)), the base sequences of the SOX1 gene are publicly known (NCBI accession Nos. NM_005986 (human) and NM_009233 (Mouse)), the base sequences of the SOX3 gene are publicly known (NCBI accession Nos. NM_005634 (human) and NM_009237 (Mouse)), the base sequences of the SOX7 gene are publicly known (NCBI accession Nos. NM_031439 (human) and NM_011446 (Mouse)), the base sequences of the SOX15 gene are publicly known (NCBI accession Nos. NM_006942 (human) and NM_009235 (Mouse)), the base sequences of the SOX17 are publicly known (NCBI accession Nos. NM_022454 (human) and NM_011441 (Mouse)), and the base sequences of the SOX18 gene are publicly known (NCBI accession Nos. NM_018419 (human) and NM_009236 (Mouse)).

(KLF Family)

The nuclear reprogramming substance can further include the gene belonging to the KLF family. The gene in the KLF family can be a KLF1 gene, a KLF2 gene, a KLF4 gene, a KLF5 gene, or the like. These genes in the KLF family may be used alone or in a combination of two or more of them. From the viewpoint of the efficient induction of iPS cells, the KLF4 gene is favorably used among the genes in the KLF family. The base sequences of the KLF4 gene are publicly known (NCBI accession Nos. NM_004235 (human) and NM_010637 (Mouse)). Moreover, the base sequences of the KLF1 gene are publicly known (NCBI accession Nos. NM_006563 (human) and NM_010635 (Mouse)), the base sequences of the KLF2 gene are publicly known (NCBI accession Nos. NM_016270 (human) and NM_008452 (Mouse)), and the base sequences of the KLF5 gene are publicly known (NCBI accession Nos. NM_001730 (human) and NM_009769 (Mouse)).

As the nuclear reprogramming substance, a gene in OCT family such as a OCT3/4 gene, and a gene in SOX family such as a SOX2 gene are preferably used in combination with the DLX4 gene. More preferably, a gene in the KLF family such as a KLF4 gene is further used in combination. Such combination is suitable for use of iPS cells in treatment of human or the like. On the other hand, in the case of leaving the use of IPS cells in treatment out of consideration (for example, the case of using iPS cells as a research tool such as screening for drug discovery), a gene in the LIN family such as Lin28 is preferably used in addition to the DLX4 gene, the gene in OCT family such as an OCT3/4 gene, the gene in the SOX family such as an SOX2 gene, and the gene in the KLF family such as a KLF4 gene. Furthermore, using six factors including a Nanog gene is also preferable.

Information on mouse and human cDNA sequences of the Nanog gene can be obtained with reference to the NCBI accession numbers described in WO2007/069666 (in the publication, the Nanog gene is described as "ECAT4"; information on mouse and human cDNA sequences of the Lin28 gene can be obtained with reference to the NCBI accession Nos. NM_145833 and NM_024674), and a person skilled in the art can easily isolate these cDNAs.

The genes include homologous genes thereof. Each homologous gene means a gene which encodes a protein having the same function as a protein which is encoded by the gene. The gene generally has a DNA composed of a base sequence having a homology of at least 70% or more, preferably 80% or more, more preferably 90% or more, yet more preferably 91% or more, yet more preferably 92% or more, yet more preferably 93% or more, yet more preferably 94% or more, yet more preferably 95% or more, yet more preferably 96% or more, yet more preferably 97% or more, yet more preferably 98% or more, yet more preferably 99% or more to the base sequence of each gene.

The protein which is encoded by the homologous gene has a peptide chain composed of an amino acid sequence having a homology of at least 70% or more, preferably 80% or more, more preferably 90% or more, yet more preferably 91% or more, yet more preferably 92% or more, yet more preferably 93% or more, yet more preferably 94% or more, yet more preferably 95% or more, yet more preferably 96% or more, yet more preferably 97% or more, yet more preferably 98% or more, yet more preferably 99% or more to the amino acid sequence of the protein which is encoded by the gene. Moreover, each gene may be the same or different kind of gene to the cell. A person skilled in the art can obtain these genes of necessary animal species by searching a database.

"Identity" and "similarity" herein, as have been known well to those skilled in the art, are relationships between two or more proteins or two more polynucleotide determined by comparing the sequences. "Identity" in the art, also means the degree of sequence invariance between protein or polynucleotide sequences, as determined by the alignment between the protein or polynucleotide sequences, as the case maybe the alignment between strings of such sequences. In addition, "similarity" means the degree of sequence relatedness between protein or polynucleotide sequences, as determined by the alignment between the protein or polynucleotide sequences, as the case maybe the alignment between strings of such sequences. More specifically, "Similarity" is determined by the sequence identity or conservativeness (replacement which can maintain the physical and chemical properties of a particular amino acid or amino acid sequence). "Similarity" is referred to as similarity in the search result BLAST sequence homology to be described later. Preferred methods of determining "identity" or "similarity" are designed to give the longest alignment between the sequences to be tested. Method for determining identity and similarity, are codified in publicly available computer programs. "Identity" and "similarity" can be determined by, for example, using the BLAST (Basic Local Alignment Search Tool) program by Altschul et. al., (for example, Altschul S F, Gish W, Miller W, Myers E W, Lipman D J, J. Mol Biol, 215: P 403-410 (1990), Altschyl S F, Madden T L, Schaffer A A, Zhang J, Miller W, Lipman D J, 25 Nucleic Acids Res. 25: p 3389-3402 (1997)). Where software such as BLAST used, it is but not limited to, preferable to use default values.

Stringent condition refers to conditions, for example in which so-called specific hybrid is formed, anon-specific hybrid is not formed. For example, a condition such that the complementary strand of the DNA or the part thereof having high identity such as at least 80% identical, preferably at least 85% identity, more preferably at least 90%, or still more preferably at least 95%, further more preferably at least 98%, or most preferably at least 99% identity with the predetermined sequence hybridizes with the DNA while the complementary strand or the part thereof having the lower identity does not hybridize with the DNA is included. Typically, sodium salt concentration is 15 to 750 mM, preferably 50 to 750 mM, more preferably 300 to 750 mM, temperature is 25 to 70° C., preferably 50 to 70° C., more preferably 55° to 65° C., and formamide concentration is 0 to 50%, preferably 20 to 50%, more preferably 35 to 45%. Further, stringent condition includes filter washing condition after hybridization which sodium salt concentration is 15 to 600 mM, preferably 50 to 600 mM, more preferably 300 to 600 mM and temperature is 50 to 70° C., preferably 55 to 70° C., more preferably 60° to 65° C., typically. Accordingly, further embodiments of the terminator region include terminator region having high identity such as at least 80% identical, preferably at least 85% identity, more preferably at least 90%, or still more preferably at least 95%, further more preferably at least 98%, or most preferably at least 99% identity with the predetermined terminator region.

Another aspect of the nuclear reprogramming substance can be a translation product of the DLX 4 gene, a translation product of the gene belonging to the OCT family such as a OCT3/4 gene, or a translation product of the gene belonging to the SOX family such as an SOX2 gene. Another aspect of the nuclear reprogramming substance can further be a translation product of the gene belonging to the KLF family such as a KLF4 gene. The translation product of each gene intends a protein.

For example, as the DLX4 protein, a human-derived DLX4 protein having an amino acid sequence represented by SEQ ID NO: 2 can be used. Moreover, as the mouse-derived DLX4 protein, a protein having an amino acid sequence represented by SEQ ID NO: 4 can be used.

The nuclear reprogramming substance may be another protein having the same function as the translation product of each gene. The protein having the same function generally has a peptide chain composed of an amino acid having a homology of at least 70% or more, preferably 80% or more, more preferably 90% or more, yet more preferably 91% or more, yet more preferably 92% or more, yet more preferably 93% or more, yet more preferably 94% or more, yet more preferably 95% or more, yet more preferably 96% or more, yet more preferably 97% or more, yet more preferably 98% or more, yet more preferably 99% or more to the amino acid sequence of a specific protein.

The protein having the same function includes a protein which exerts ability superior to wild-type differentiation pluripotency induction ability. The protein which exerts such superior ability can be prepared by modification such as deletion, substitution, or addition of an amino acid sequence of a wild-type protein by a known method in this technical field. In the modification, for example, the substitution of a specific amino-acid residue can be made by an appropriate base substitution of a gene of a differentiation pluripotency factor by a known method such as Gapped duplex method or Kunkel method or a method according thereto using a commercially-available kit (for example, MutanTM-G (TaKaRa), MutanTM-K (TaKaRa)) or the like.

As the nuclear reprogramming substance, only the gene may be used, or only a translation product thereof may be used, and a combination of the gene and the translation product thereof may be used.

In the case of using a protein as the nuclear reprogramming substance, the protein can be prepared by inserting an isolated cDNA into an appropriate expression vector to transfect into a host cell, then cultivating the cell, and recovering a recombinant protein from the obtained culture.

(iPS Cell Induction Efficiency Improving Substance)

In the present specification, a known induction efficiency improving substance may be used in addition to the nuclear reprogramming substance. Examples of the iPS cell induction efficiency improving substance include a histone deacetylase (HDAC) inhibitor (for example, a low-molecular-weight molecule inhibitor such as valproic acid (VPA) (Nat. Biotechnol., 26(7): 795-797 (2008)), trichostatin A, sodium butyrate, MC 1293, or M344, an nucleic acid expression inhibitor such as siRNA or shRNA to HDAC (for example, HDAC1 siRNA Smartpool (registered trademark) (Millipore) or HuSH 29mer shRNA Constructs against HDAC1 (OriGene)), or a G9a histone methyltransferase inhibitor (for example, a low-molecular-weight molecule inhibitor such as BIX-01294 (Cell Stem Cell, 2: 525-528 (2008)) or a nucleic acid expression inhibitor such as siRNA or shRNA to G9a (for example, G9a siRNA (human) (Santa Cruz Biotechnology)). However, the induction efficiency reprogramming substance is not limited to these. The nucleic acid expression inhibitor may be in a form of an expression vector including a DNA which encodes siRNA or shRNA.

The contact of the iPS cell induction efficiency improving substance with the cell can be performed by any of the methods described above for the nuclear reprogramming substances, according to each of the cases where the substance is (a) a proteinaceous factor, (b) a nucleic acid which encodes the proteinaceous factor, and (c) a low-molecular-weight compound.

(Recombinant Vector)

In order to supply each gene which is the nuclear reprogramming substance and the induction efficiency improving substance to a cell, a recombinant vector is used. Each gene is transfected into an appropriate vector including a promoter which can function in a cell which can be a host. As the vector, for example, a virus vector such as a retrovirus vector, an adenovirus vector, an adeno-associated virus vector, a vaccinia virus vector, a lentivirus vector, a herpesvirus vector, an alphavirus vector, an EB virus vector, a papillomavirus vector, or a foamy virus vector or an animal cell expression plasmid (for example, pA1-11, pXT1, pRc/CMV, pRc/RSV, pcDNAI/Neo) can be used. The kind of the vector to be used can be selected as appropriate according to the use of iPS cells to be obtained. The genes may be transfected into one vector or two or more vectors separately.

As the promoter used in the vector, for example, an SRα promoter, an SV40 promoter, an LTR promoter, a CMV (cytomegalovirus) promoter, an RSV (Rous sarcoma virus) promoter, a MoMuLV (Moloney murine leukemia virus) LTR, an HSV-TK (herpes simplex virus thymidine kinase) promoter, or the like is used. Among them, the MoMuLV LTR, the CMV promoter, the SRα promoter, or the like is preferable. The vector may contain an enhancer, a poly-A addition signal, a selection marker gene, SV40 ori, and the like if desired in addition to the promoter. Examples of the selection marker gene include a dihydrofolate reductase gene and a neomycin resistance gene.

A terminator used in the vector is a polyadenylation signal as a transcription termination sequence. Although it is not limited, examples of the sequence of the polyadenylation signal include human BGH poly A, SV40 poly A, human β actin poly A, rabbit β globulin poly A, and immunoglobulin κ poly A.

(Vector Set)

As mentioned above, each gene is transfected into one or two or more vectors. The present specification discloses a vector set containing one or two or more recombinant vectors into which the genes are transfected. That is, the vector set may be a recombinant vector or a mixture of two or more recombinant vectors. When all of the genes are contained in the vector set containing two or more recombinant vectors, the ratio of the number of the recombinant vectors does not matter. However, the ratio of the number of the recombinant vectors is preferably set so as to contain the same amounts of the genes.

(Cell)

In the present specification, a somatic cell which can be used as a starting material for producing iPS cells may be any cell other than germ cells derived from mammals (for example, a mouse or human). Examples of the somatic cell include a keratinizing epithelial cell (for example, a keratinizing epidermal cell), a mucosa epithelial cell (for example, an epithelial cell of tongue surface), an exocrine gland epithelial cell (for example, a mammary cell), a hormone secreting cell (for example, an adrenomedullary cell), a cell for metabolism and storage (for example, a liver cell), a luminal epithelial cell composing a boundary surface (for example, an I-type alveolar cell), a luminal epithelial cell of inner vessel (for example, vascular endothelial cell), a cell having the cilium which has a carrying capacity (for example, tracheal epithelial cell), a cell for secretion of extracellular matrix (for example, fibroblast), constrictive cell (for example, a smooth muscle cell), a blood cell and an immune cell (for example, T lymphocyte), a sensory-relating cell (for example, a rod cell), a autonomic nervous neuron (for example, a cholinergic neuron), sustentacular cells of a sense organ and a peripheral nerve (for example, an associated cell), a central nervous system neuron and a glial cell (for example, a stellate glial cell), a pigment cell (for example, a retinal pigment epithelial cell), and progenitor cells thereof (tissue progenitor cells). The extend of the differentiation of the cell is not particularly limited, both of an undifferentiated progenitor cell (including a somatic stem cell) and a terminal-differentiated mature cell can be used as the origin of the somatic cell in the present invention. Examples of the undifferentiated progenitor cell include tissue stem cells (somatic stem cells) such as a neural stem cell, a hematopoietic stem cell, a pulpal stem cell, and a mesenchymal stem cell. As the cell, a cell having a high expression level of DLX4 gene is used. The cell having a high expression level of DLX4 gene can be, for example, DPC, specifically DPC before the stage of completion of tooth root formation.

The cell used in the present specification may be derived from any animal species (including mammals) which can induce iPS cells by bringing a nuclear reprogramming substance into contact with the cell. Specifically, the cell can be derived from human or a mouse and is preferably a cell derived from human. The cell can be collected from any animal species. However, in the case where the resultant iPS cells are in regenerative medicine for human, the cell is particularly preferably collected from the patient or another person having the homogeneous HLA from the viewpoint of avoiding rejection. Even when iPS cells are not administered (transplanted) into human, for example, in the case of using iPS cells as a source of cells for screening for evaluating the presence or absence of drug sensitivity and adverse effect in a patient, the cells are required to be collected from the patient or another person having the same gene polymorphism correlated with drug sensitivity or an adverse effect.

(DPC (Dental Pulp Cell, Pulp Cell))

DPC is a cell group of connective tissue abounding with blood vessels and neurons in the cadre of tooth. In the present invention, DPC means a cell group specified by an anatomical position of such biological body.

A method for obtaining DPC derived mainly from human is described below.

DPC can be collected by a method known in this art. DPC is particularly preferably derived from a tooth obtained by extraction according to a dental treatment or an object separated from gingiva together with tooth at the time of extraction. In many cases, the extraction is performed due to an abnormality/problem in tooth. Thus, a pulp cell itself available according to the extraction retains the properties of the cell. Therefore, it is advantageous to use such pulp cell.

As DPC, using DPC of youth (the age of about 16 or less, although there are individual differences) is preferable. In some cases, a wisdom toot is extracted for orthodontics at the age of 12-16. Thus, by employing such method of obtaining the cell, a pulp cell which has been a waste can be effectively used. Moreover, a desired cell can be obtained without an "additional treatment" for obtaining the cell.

In the case were collected tooth-relating cell contains a connective tissue and a debris, they can be removed using an appropriate enzyme, for example, Dispase or trypsin, or a nylon mesh.

The growth stages of DPC include the stage of the completion of tooth crown formation, the stage of the formation of tooth root, and the stage of the stage of the completion of tooth root formation. In the present specification, using DPC before the stage of the completion of tooth root formation is preferable. The tooth crown is a portion actually erupted from gingiva in the oral cavity, the topmost surface thereof is enamel, and the inside thereof is dentinal. The tooth root is a portion buried in gingiva, and the topmost surface thereof is cementum, and the inside thereof is dentinal. The stage of the completion of tooth crown is a stage in which hard tissues such as the enamel and the dentin are formed, and the stage of tooth root formation is a stage in which cementum is formed, i.e., a stage in which a tooth root is formed, and the stage of the stage of the completion of tooth root formation is a stage in which a tooth root is formed completely. These growth stages can be distinguished by taking an X-ray photograph.

The preferred DPC can be distinguished by the expression level of DLX4 gene. For example, the expression level of DLX4 gene by DPC cultivated under the same conditions as the homogeneous skin fibroblast is preferably 200 times or more, more preferably 300 times or more, yet more preferably 500 times or more, yet more preferably 800 times or more, yet more preferably 1000 times or more, the expression level of the skin fibroblast. Moreover, the expression level of the DLX4 gene by DPC cultivated under the same conditions as the homogeneous ES cell is preferably 50% or more to 200% or less of the expression level of the ES cell. As such conditions of the cultivation, the conditions of the cultivation of the embodiments described below can be employed.

As mentioned above, DPC is characterized by having a high expression level of DLX4 gene. Specifically, DPC before the stage of the completion of tooth root formation (i.e., the stage of the completion of tooth crown formation or the stage of tooth root formation) is higher than the expression level of the DLX4 gene by DPC in the stage of the completion of tooth root formation and is favorably used as a cell for transfecting the genes. DPC before the stage of the completion of tooth root formation can be collected from youth (the age of about 16 or less). The use of the DLX4 gene derived from DPC (i.e., endogenous DLX4 gene) causes an increase in iPS cell induction efficiency, compared with the use of the exogenous DLX4 gene.

A pulp cell prepared from tooth which is obtained by extraction or natural avulsion by the above-mentioned method may be immediately brought into contact with a nuclear reprogramming substance to induce iPS cells or cryopreserved by the usual method, thawed before use and cultivated, and thereafter caused to bring into contact with a nuclear reprogramming substance to induce iPS cells. Therefore, for example, it is possible to cryopreserve a pulp cell prepared from a primary tooth of a patient or a primary tooth or a wisdom tooth extracted in the relatively early file of the patient, for a long period of time, induce iPS cells from the pulp cell at the time when the cell/organ transplantation is required in later years, and homogeneous transplant a cell, a tissue, an organ, or the like, obtained by induction of differentiation into the patient.

The pulp cell can be prepared from a tooth or a wisdom tooth extracted by a surgery for orthodontics or a tooth or a wisdom tooth extracted for dental caries, pericoronitis of the wisdom tooth, or the like, and pulp cells of many people can be collected easily.

(iPS Cell Production Agent)

The present specification also discloses an iPS cell production agent containing the vector set, an agent for producing iPS cells including a pulp cell before the stage of completion of tooth root formation, and an iPS cell production agent containing a DLX4 gene. These iPS cell production agents may be combined to produce an iPS cell production agent.

(Method for Producing iPS Cells)

The present specification provides a method for producing iPS cells. The method includes a step of bringing a nuclear reprogramming substance into contact with a cell.

(Step of Bringing Nuclear Reprogramming Substance into Contact with Cell)

In the step of bringing a nuclear reprogramming substance into contact with a cell, a nuclear reprogramming substance is brought into contact with a cell, so that the nuclear reprogramming substance can be in the state of being transfected into the cell. Thus, iPS cells can be induced. In the step, in the case where the nuclear reprogramming substance is genes, each gene is integrated into a vector, and the vector can be transfected into the cell directly or via a virus. On the other hand, in the case where the nuclear reprogramming substance is a protein, the protein can be transfected into the cell by a known protein transfection method. The method for bringing a nuclear reprogramming substance into contact with a cell is described in detail below.

(Contact of Vector with Cell)

The vector containing genes which is the nuclear reprogramming substance can be transfected into the cell by bringing it into contact with the cell by a publicly known method according to the kind of the vector. For example, in the case where the vector is a virus vector, a plasmid containing the nucleic acid is transfected into an appropriate packaging cell (for example, a Plat-E cell) and a complementary cell line (for example, 293 cell), a virus vector generated in a culture supernatant is recovered, and the vector is infected into the cell by an appropriate method according to each virus vector. On the other hand, in the case where the vector is a plasmid vector, the vector can be transfected into the cell using a lipofection method, a liposome method, an electroporation method, a calcium phosphate co-precipitation method, a DEAE dextran method, a microinjection method, a gene gun method, or the like.

(Contact of Protein as Nuclear Reprogramming Substance with Cell)

In the case where the nuclear reprogramming substance is a protein, the contact of the nuclear reprogramming substance with the cell can be performed using a publicly known method for transfecting a protein into a cell. Examples of such method include a method using a protein transfection reagent, a method using a protein transfection domain (PTD) fusion protein, and a microinjection method. As the protein transfection reagent, a bioPOTER Protein Delivery Reagent (GeneTherapy Systems), a Pro-JectT M Protein Transfection Reagent (PIERCE), and ProVectin (IM-GENEX), based on a cationic lipid, a Profect-1 based on a lipid (Targeting Systems), and Penetrain Peptide (Q biogene) and a Chariot Kit (Active Motif), based on a cell-penetrating peptide, and the like are commercially available. The transfection can be performed according to protocols attached to these reagents, and general procedures are as follows. A nuclear reprogramming substance is diluted with an appropriate solvent (for example, a buffer solution such as PBS or HEPES), a transfection reagent is added to the resultant solution, and the solution is incubated at room temperature for about 5 to 15 minutes, to form a complex. This complex is added to a cell in a serum-free medium and is incubated at 37° C. for one to several hours. Thereafter, the medium is removed, and the complex is transfected into a serum-containing medium.

As PTD, a transcellular domain of a protein such as AntP derived from *Drosophila*, TAT derived from HIV, or VP22 derived from HSV has been developed.

The cell can be pre-cultured in a publicly known medium which is appropriate for the cultivation (for example, see Japanese Translation of PCT Application No. H11-506610, Japanese Translation of PCT Application No. 2000-51502; Mesenchymal stem cells basal medium (Lonza), MesenPRO RS Medium (GIBCO), and the like are commercially available). For example, the cell can be pre-cultured also in a minimum essential medium (MEM) containing about 5% to 20% of fetal bovine serum, a Dulbecco's modified Eagle's medium (DMEM), a RPMI1640 medium, a 199 medium, a F12 medium, or the like.

For example, when a transfection reagent such as a cationic liposome is used at the time when the nuclear reprogramming substance (or the induction efficiency improving substance of iPS cells) is brought into contact with the cell, the cell is preferably transfected into a serum-free medium in order to prevent the reduction in transfection efficiency in some cases. The nuclear reprogramming substance (or the induction efficiency improving substance of iPS cells) is brought into contact with the cell, and thereafter, the cell can be cultured under the conditions which are appropriate for cultivation of ES cells, for example. In the case where the cell is a human cell, the cell is cultured in a general medium to which a basic fibroblast growth factor (bFGF) as a differentiation inhibitory factor has been added. On the other hand, in the case where the cell is a mouse cell, a Leukemia Inhibitory Factor (LIF) is desirably added as a substitute for bFGF. Generally, the cell as a feeder cell is cultured in the presence of mouse embryo-derived fibroblast (MEF) which has been treated with radiation or antibiotic to stop cell division. As the MEF, an STO cell or the like is generally used often. However, in order to induct iPS cells, an SNL cell (McMahon, A. P. & Bradley, A. Cell 62, 1073-1085 (1990)) or the like is often used.

The selection of a candidate colony of iPS cells can be performed by a method using a drug resistance and a reporter activity as indicators or a method of morphology observation by visual check. In the former, for example, in the gene locus of a gene which specifically highly express in a differentiation pluripotency cell (for example, a OCT3/4 gene), a recombinant cell targeting a drug resistance gene and/or a reporter gene is used, and a drug resistance and/or reporter activity positive colony is selected. On the other hand, the method for selecting a candidate colony by morphology observation by a visual check can be, for example a method descried in Takahashi et al., Cell, 131, 861-872 (2007). The method using a reporter cell is simple and efficient. However, in the case where iPS cells are used for a treatment of human, the selection of a colony by a visual check is desirable from the viewpoint of safety. In the case where three factors of a DLX4 gene, an OCT3/4 gene, and an SOX2 gene are used as a nuclear reprogramming substance, the number of induced clones is decreased and however, most of generated colonies are iPS cells having high quality which is almost equivalent of ES cells. Thus, iPS cells can be induced efficiently without using a reporter cell. Specifically, the present invention brings about an action effect of significantly improving the iPS induction efficiency by transfection of the three factors. Thus, a candidate colony of iPS cells can be sufficiently efficiently selected by morphology observation by visual check.

Whether or not cells of the selected colony are iPS cells can be checked by publicly known various test method such as, for example, ES cell-specific gene expression analysis and the like. For the accuracy, the selected cells are transplanted into a mouse, and formation of teratoma may be checked.

The iPS cells produced by the step of bringing a nuclear reprogramming substance into contact with a cell can be used for various purposes. For example, by using a differentiation induction method reported for ES cells, differentiations of iPS cells into various cells (for example, a myocardial cell, a retinal cell, a blood cell, a neuron, a vascular endothelial cell, an insulin-secreting cell, and the like), tissues, and organs can be induced.

EMBODIMENTS

The present invention is described in detail below with reference to the embodiments. These embodiments do not limit the present invention.

First Embodiment (Evaluation of iPS Cell Induction Efficiency in Various DPC Lines)

In order to determine the induction efficiency of various DPCs, four types of an OCT3/4 gene, an SOX2 gene, a KLF4 gene, and a c-MYC gene were transfected into each of nines types of DPC lines (DP1, DP31, DP75, DP87, DP94, DP133, DP165, DP166, and DP193) to produce iPS cells. The iPS cells were produced as follows.

Pulp cells were prepared from teeth extracted from 14-year-old to 60-year-old humans (DP1, DP31, DP75, DP87, DP94, DP133, DP165, DP166, and DP193). Specifically, dental pulp tissues were extirpated from wisdom teeth extracted from patients with orthodontics or pericoronitis of the wisdom tooth, where then cut by an ophthalmologic cooper so as to be tissue slices each with a size of about 1 to 2 mm, and thereafter treated with a Collagenase type I (1 mg/me at 37° C. for 0.5 to 1 hour. This was then cultivated in a Mesenchymal stem cells basal medium (Lonza). Thus, cell lines of the pulp cells were established.

A mouse ecotropic virus receptor-Slc7a1 gene was expressed in these cells ($8 \times 10^5$ cells) according to a method described in Cell, 131, 861-872 (2007) using lentivirus.

Four factors (Oct3/4, Sox2, Klf4, and c-Myc) derived from human were transfected into these cells with retrovirus in the presence of 4 μg/ml polybrene (hexadimethylene bromide) according to a method described in Cell, 131, 861-872 (2007). The cells were collected 6 days after the virus infection and were re-plated on feeder cells ($5 \times 10^4$ cells or $5 \times 10^5$ cells/100 mm dish). As the feeder cells, SNL cells which had been treated with mitomycin C to stop cell division (McMahon, A. P. & Bradley, A. Cell 62, 1073-1085 (1990)) were used. The cells were cultivated in a medium obtained by adding 4 ng/ml recombinant human bFGF (WAKO) to a primate ES cell medium (ReproCELL) from the next day.

21 days after the virus infection, ES cell-like colonies obtained from infected $5 \times 10^4$ DPCs were morphologically determined, and the number of the colonies was counted. The evaluation was performed three times, and the average of the numbers of the ES cell-like colonies of each DPC was calculated and was normalized by the average obtained from DP31. The relative induction efficiency of DP31 was regarded as 1.0. The results are shown in FIG. 1.

As shown in FIG. 1, DP1, DP31, DP87, and DP94 were DPCs in the stage of the completion of tooth crown formation or the stage of tooth root formation (i.e., the stage of the completion of tooth root formation), and DP75, DP133, DP165, DP166, and DP193 were DPCs after the stage of the completion of tooth root formation. It was demonstrated that the DPCs before the stage of the completion of tooth root formation showed higher induction efficiency than the DPCs after the stage of the completion of tooth root formation.

Second Embodiment (Evaluation of Gene Expression Level in DPC)

Figure 2:
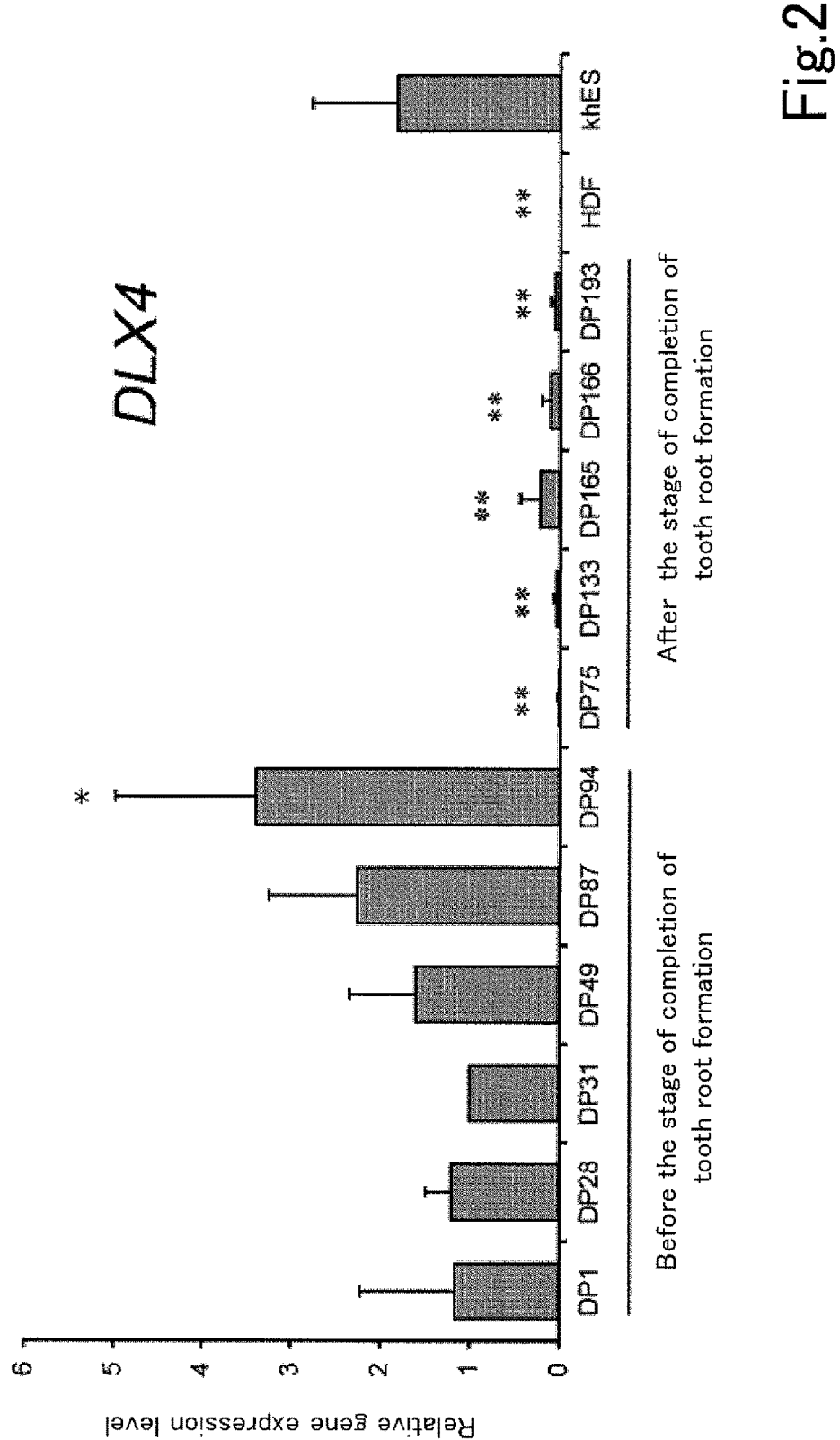
FIG. 2 shows the result of relative DLX4 gene expression level in each DPC.

In addition to the DPCs evaluated in the first embodiment, the gene expressions of fibroblast (HDF) derived from 36-year-old adult skin and human ES cell (khES) as controls were evaluated. The khES was acquired from the Institute for Frontier Medical Sciences, Kyoto University. The expression levels of the genes obtained from the DPCs, HDF, and the human ES cell (khES) were evaluated by Real-time PCR. Specifically, total RNAs of the DPCs, HDF, and the human ES cell (khES) were collected using an RNeasy Plus Mini Kit (Qiagen). cDNA was synthesized from each of the total RNA (500 ng) using Rever Tra Ace-α (Toyobo). The PCR reaction was carried out by a Thermal Cycler Dice Real Time System (Takara) using SYBR Premix Ex Taq (Takara) and primer DLX4 (S) (SEQ ID NO: 5) and DLX4 (AS) (SEQ ID NO: 6) (Takara) designed for each gene. The expression levels were analyzed using a Thermal Cycler Dice Real Time System. Plural genes before the stage of the completion of tooth root formation showed fluctuations in the number of genes, and among them, the results of DLX4 genes are shown in FIG. 2. In FIG. 2, the expression levels normalized by the expression level of DLX4 gene obtained from DP31 are shown. The relative expression level in DP31 was regarded as 1.0.

DLX4 (S):
(SEQ ID NO: 5)
TAA ACC AGC GTT TCC AGC AC

DLX4 (AS):
(SEQ ID NO: 6)
CTT ATA CTT GGA GCG TTT GTT CTG A

As shown in FIG. 2, it was demonstrated that the relative expression level of DLX4 gene in each of DPCs before the stage of the completion of tooth root formation was high, compared with the DPCs after the stage of the completion of tooth root formation. For example, the expression levels were about 11 to about 37 times higher than the average of the expression levels of DPCs after the stage of the completion of tooth root formation. Compared with DP31, the HDF barely showed a DLX4 gene expression. It was demonstrated that the DPCs before the stage of the completion of tooth root formation showed expression levels about 340 to about 1100 times higher than the HDF.

Moreover, it was demonstrated that, compared with the khES, the DPCs before the stage of the completion of tooth root formation showed almost the same relative expression level of DLX4 gene (about 60% to about 190%).

As described above, it was demonstrated that the expression of the DLX4 gene was significantly accelerated in the DPC before the stage of the completion of tooth root formation.

Third Embodiment

The involvement of the DLX4 gene in which the acceleration of the expression was observed in DPC before the stage of the completion of tooth root formation in the iPS cell induction efficiency was evaluated.

In the present embodiment, DP31 which is DPC used in the first embodiment was used. As a control, 36-year-old adult skin-derived fibroblast (HDF) was used.

(Production of Vector)

Figure 3:
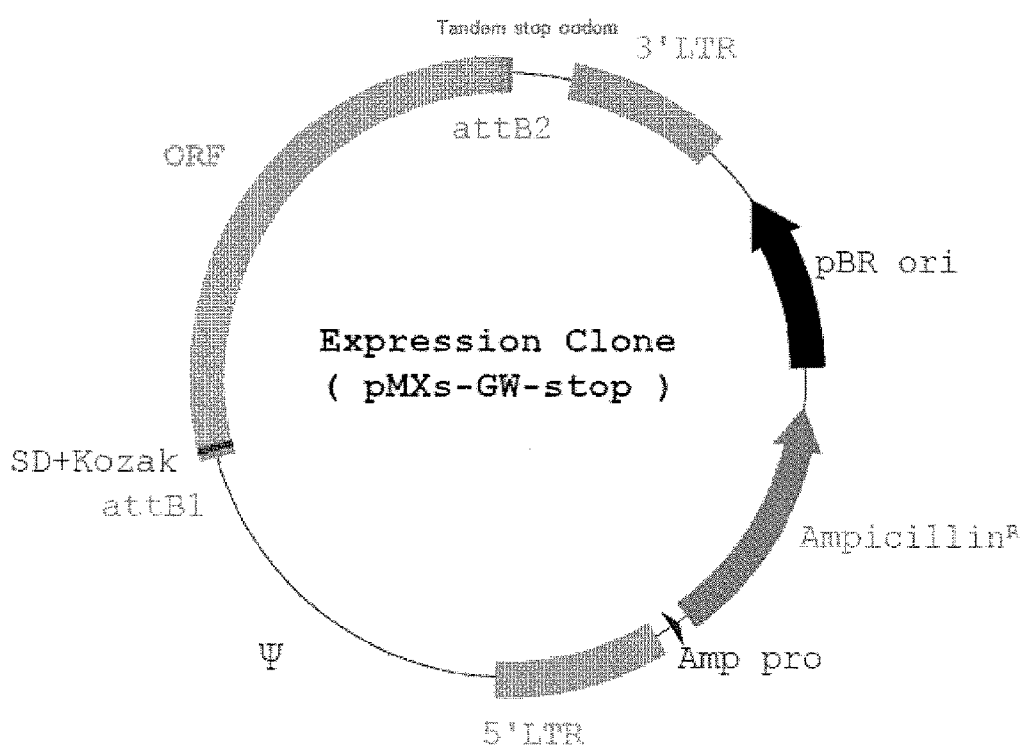
FIG. 3 shows a vector map of pMXs-GW retrovirus vector.

A recombinant pMXs-GW retrovirus vector (hereinafter referred to as a DLX4 vector) was produced by transfecting a DLX4 gene (SEQ ID NO: 1) derived from human into an ORF region of a pMXs-GW retrovirus vector shown in FIG. 3, using a Gateway (registered trademark) LR reaction.

The DLX4 vector and a pMXs vector retaining an OCT3/4 gene, a pMXs vector retaining an SOX2 gene, and a pMXs vector retaining a KLF4 gene which were acquired separately were combined as appropriate, and the combinations were transfected into Plat-E cells (ecotropic retrovirus packaging cells) using Fugene6 (Roche).

Accordingly, the following five types of Plat-E cells retaining genes so as to be infected were prepared.
(1) A Plat-E cell 1 into which an OCT3/4 gene and an SOX2 gene (OS) is transfected
(2) Plat-E cell 2 into which an OCT3/4 gene, an SOX2 gene, and a DLX4 gene (OSD) is transfected (3) Plat-E cell 3 into which an OCT3/4 gene, an SOX2 gene, and a KLF4 gene (OSK) is transfected
(4) Plat-E cell 4 into which an OCT3/4 gene, an SOX2 gene, a KLF4 gene, and a DLX4 gene (OSKD) is transfected
(5) Plat-E cell 5 (OSKM) into which an OCT3/4 gene, an SOX2 gene, a KLF4 gene, and a c-MYC gene is transfected.

Subsequently, the gene transfection efficiency of each of the various Plat-E cells were monitored according to fluorescence active cell analysis using a BD FACSAria cell sorter (Beckton Dickinson) using a pMXs vector which encodes an EGFP (enhanced green fluorescent protein).

Thereafter, virus supernatants were recovered from the various Plat-E cells and were infected with DP31 and HDF in the same manner as in the first embodiment, the ES cell-like (iPS cell) colonies appeared in each medium were determined morphologically, and the number of colonies was counted. The each number of ES cell-like colonies counted in DP31 is shown in FIG. 4.

Figure 4:
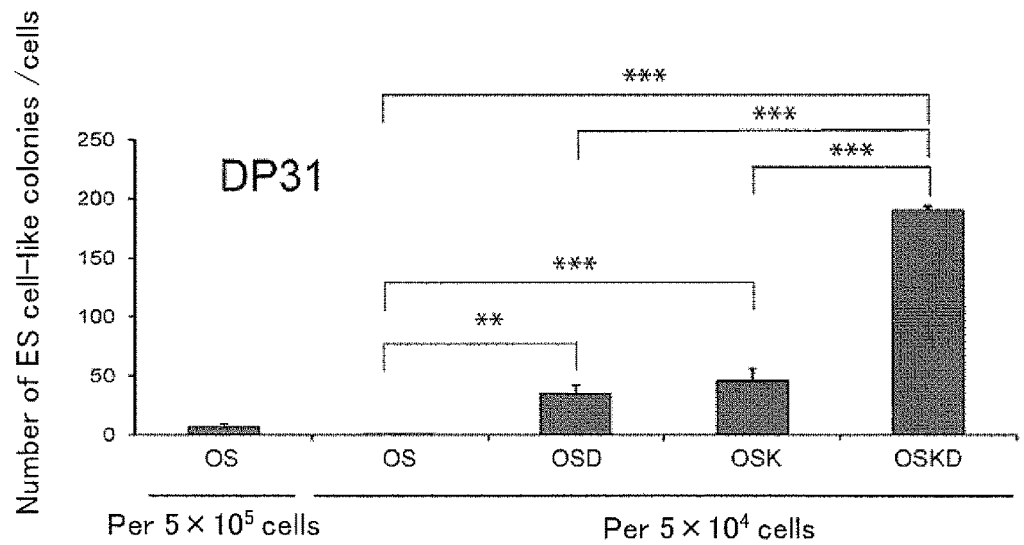
FIG. 4 shows the number of ES cell-like colonies counted in DP31 into which each gene is transfected.

As shown in FIG. 4, about 50 times ES cell-like colonies were appeared in OSD compared with OS, and about 4.3 times ES cell-like colonies were appeared in OSKD compared with OSK. These results demonstrated that the iPS cell induction efficiency was dramatically increased by adding a DLX4 gene as a nuclear reprogramming substance. That is, it was demonstrated that the DLX4 gene has almost the same induction action as the KLF4 gene. Moreover, about 5.4 times ES cell-like colonies were appeared in OSKD compared with OSD. The result demonstrated that, in the case where the nuclear reprogramming substance includes a DLX4 gene, the iPS induction efficiency was improved synergistically by further adding KLF4.

Figure 5:
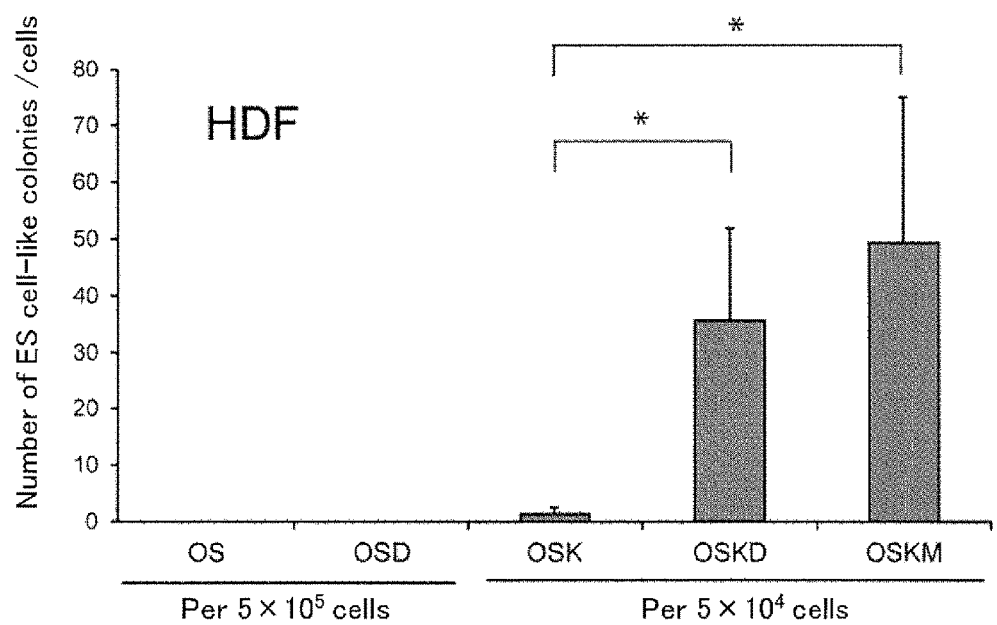
FIG. 5 shows the number of ES cell-like colonies counted in HDF into which each gene is transfected.

The each number of ES cell-like colonies counted in HDF is shown in FIG. 5. In HDF, OSKD showed the synergistically increased number of ES cell-like colonies compared with OSK. The synergistic action of the DLX4 gene and the KLF4 gene was higher in HDF compared with DP31. Moreover, there was no significant difference between the number of colonies in OSKD and the number of colonies in OSKM. That is, it was demonstrated that the DLX4 gene has the same iPS cell induction efficiency improvement effect as the c-MYC gene.

Fourth Embodiment

In the present embodiment, knockdown DPC of DLX4 gene was prepared, and the iPS cell induction effect of the DLX4 gene was checked.

(Establishment of DLX4 Knockdown DP31 Line)
Two siRNA sequences (SEQ ID NO: 7, SEQ ID NO: 8) targeting two different regions of DLX4 gene were designed. The two siRNA sequences were transfected into a pSINsi-DKI retrovirus vector (Takara) which can express two types of siRNAs, using two types of RNA polymerase III promoters (human U6 and human H1) at the same time. This siRNA-DLX4 expression retrovirus vector was transfected into a G3T-hi cell (Takara) using Retrovirus Packaging Kit Eco (Takara). After the siRNA-DLX4 expression retrovirus vector was infected, DP31/Slc cells were treated with neomycin. Thus, a stabilized siRNA-DLX4 expression DP31 was obtained.

```
siRNA-1:
                                (SEQ ID NO: 7)
GAA ACC TGG TAA AGT AAC A siRNA-2:
                                (SEQ ID NO: 8)
CGA ATT GGA GCT TGA GCT T
```

(Evaluation of DLX4 Gene Expression Level)
The DLX4 gene expression levels in DP31 and siRNA-DLX4 expression DP31 (DP31-siRNA-DLX4) were evaluated in the same manner as in the third embodiment. The expression levels obtained from these two types of cells were normalized by the expression level obtained from DP31. The relative expression level in DP31 was regarded as 1.0. The relative DLX4 gene expression levels in DP31 and DP31-siRNA-DLX4 are shown in FIG. 6.

(Evaluation of iPS Cell Induction Efficiency)
An OCT3/4 gene, an SOX2 gene, and a KLF4 gene were transfected into each of DP31 and DP31-siRNA-DLX4 in the same manner as in the first embodiment, and the same procedures as in the first embodiment were carried out. The number of colonies was not counted in the same manner as in the first embodiment and was counted after 30 days. The relative iPS cell induction efficiency in each of DP31 and DP31-siRNA-DLX4 was shown in FIG. 7.

Figure 6:
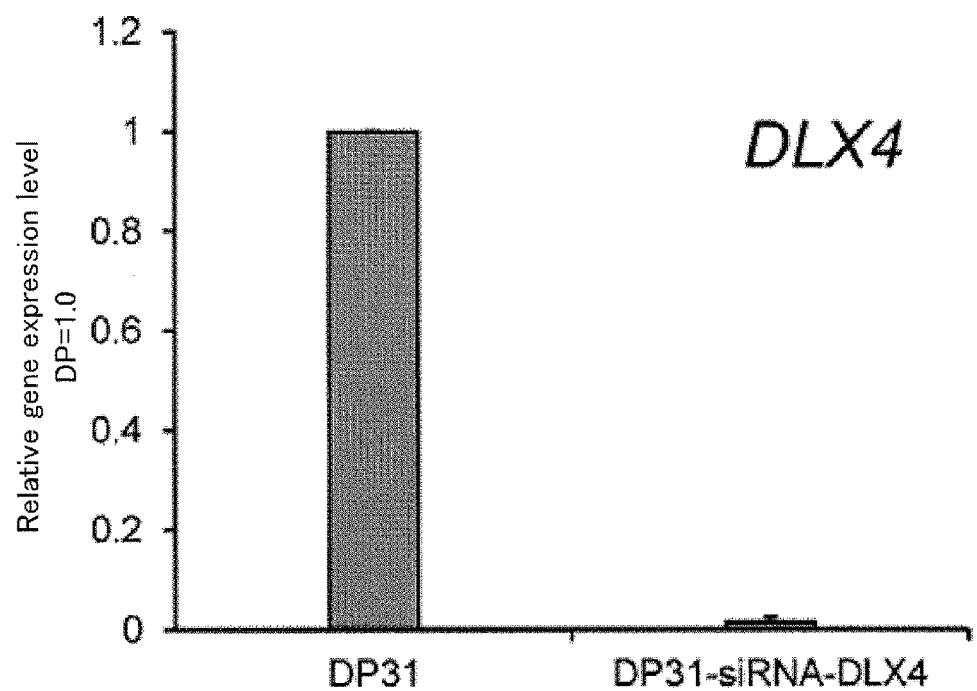
FIG. 6 shows the relative DLX4 gene expression level in each of DP31 and DP31-siRNA-DLX4.
Figure 7:
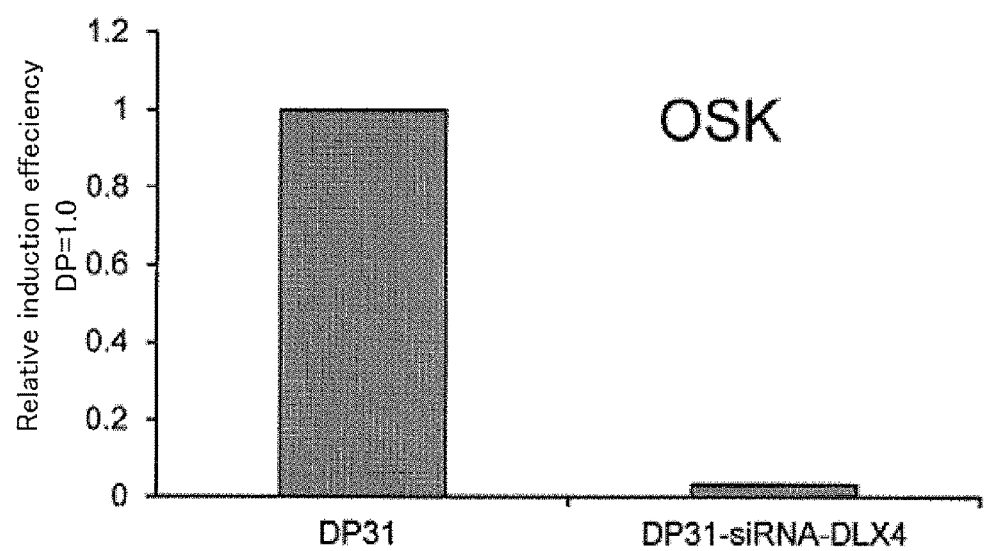
FIG. 7 shows the relative iPS cell induction efficiency in each of DP31 and DP31-siRNA-DLX4.

As shown in FIG. 6, it was demonstrated that the DXL4 gene expression level was significantly decreased in DP31-siRNA-DLX4. Moreover, as shown in FIG. 7, it was demonstrated that the iPS cell induction efficiency was significantly decreased in DP31-siRNA-DLX4. The results demonstrated that the DLX4 gene is highly involved in iPS cell induction.

Fifth Embodiment

According to the third embodiment, each of a combination (OSK) of an OCT3/4 gene, an SOX2 gene, and a KLEF4 gene and a combination (OSN) of an OCT3/4 gene, an SOX2 gene, and an NANOG gene (Addgene) were transfected into DP31, and the number of ES cell-like colonies was counted in the same manner as in the third embodiment. The results are shown in FIG. 8.

Figure 8:
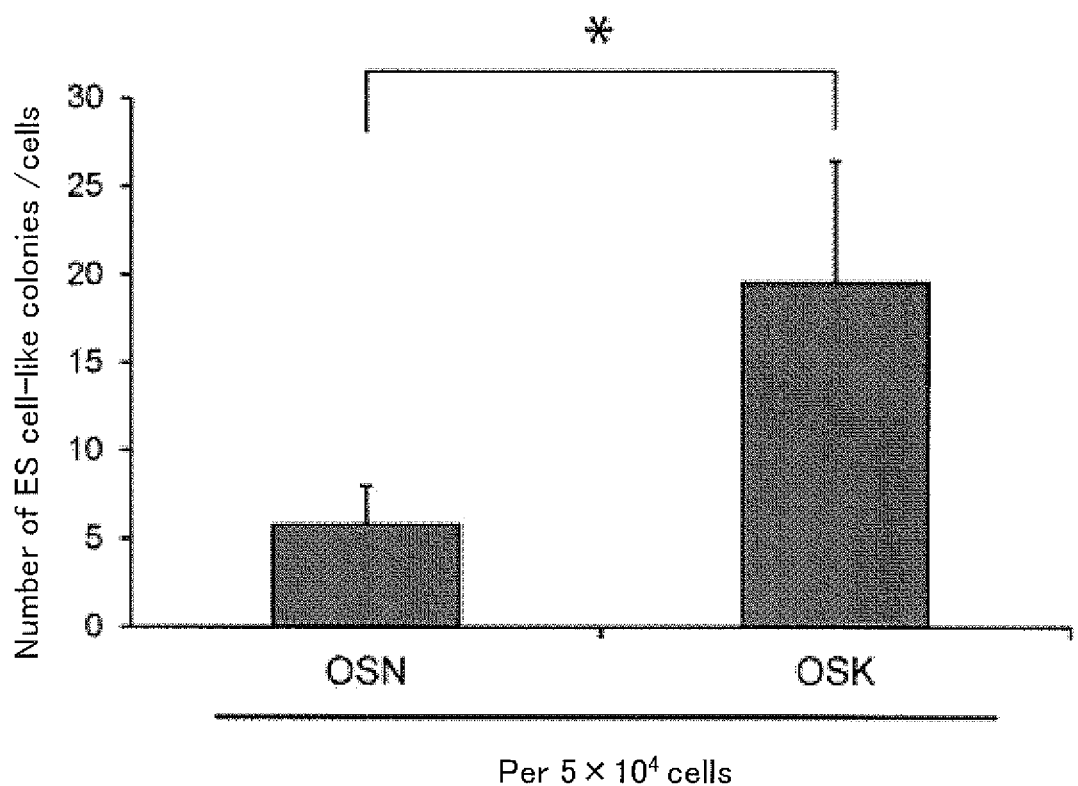
FIG. 8 shows the number of ES cell-like colonies in DP31 into which each gene is transfected.

As shown in FIG. 8, many ES cell-like colonies were appeared in OSK compared with OSN. Therefore, it was demonstrated that OSK showed higher iPS cell induction efficiency than OSN. That is, the KLF4 gene was really effective for improving the induction efficiency in DP31. As described above, it was supported that the KLF4 gene is highly involved in iPS induction efficiency compared with the NANOG gene. The DLX4 gene is naturally expressed in DP31. Thus, it can be said that the high induction efficiency in OSK shows a synergistic effect of the KLF4 gene and the DLX4 gene. Moreover, considering the results of OSK and OSKD in the third embodiment (DP31 and HDF), it was demonstrated that the DLX4 gene was really useful in that the iPS cell induction efficiency can be further improved by the synergistic action with the KLF4 gene.

Sequence Listing Free Text
SEQ ID NOs: 5 and 6: primer
SEQ ID NOs: 7 and 8: siRNA

The invention claimed is:

1. An in vitro method for producing a candidate colony of induced pluripotent stem cells, comprising:

bringing a nuclear reprogramming substance including at least a Distal-less homeobox 4 (DLX4) gene or a translation product thereof, an OCT3/4 gene or a translation product thereof, and a SOX2 gene or a translation product thereof into contact with a dental pulp cell to produce the candidate colony.

2. The method according to claim 1, wherein the nuclear reprogramming substance further includes a gene in a KLF4 family or a translation product thereof.

3. The method according to claim 2, wherein the gene in the KLF4 family or the translation product thereof is a KLF4 gene or a translation product thereof.

4. The method according to claim 1, wherein the pulp cell is a pulp cell before a stage of completion of tooth root formation.

5. The method according to claim 1, further comprising:
screening the candidate colony using morphological evaluation.

6. An in vitro method for producing a candidate colony of induced pluripotent stem cells, comprising:

bringing a nuclear reprogramming substance including at least a DLX4 gene or a translation product thereof, an OCT3/4 gene or a translation product thereof, a SOX2 gene or a translation product thereof, and a KLF4 gene or a translation product thereof into contact with a skin-derived fibroblast to produce the candidate colony.

7. The method according to claim 6, further comprising: screening the candidate colony using morphological evaluation.

* * * * *